(12) United States Patent
Macaudiere et al.

(10) Patent No.: US 6,464,953 B1
(45) Date of Patent: Oct. 15, 2002

(54) $LAMO_3$ TYPE COMPOSITION, M BEING ALUMINIUM, GALLIUM OR INDIUM, IN POWDER OR SINTERED FORM, METHOD OF PREPARATION AND USE AS CONDUCTOR OF OXYGEN

(75) Inventors: Pierre Macaudiere, Asnieres-sur-Seine (FR); Thierry Seguelong, Puteaux (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/308,538

(22) PCT Filed: Nov. 18, 1997

(86) PCT No.: PCT/FR97/02071

§ 371 (c)(1),
(2), (4) Date: Jul. 28, 1999

(87) PCT Pub. No.: WO98/22392

PCT Pub. Date: May 28, 1998

(30) Foreign Application Priority Data

Nov. 22, 1996 (FR) .............................................. 96 14276

(51) Int. Cl.⁷ ................................................ C01F 17/00
(52) U.S. Cl. ...................................... 423/263; 423/59.3
(58) Field of Search ................................. 423/263, 593

(56) References Cited

U.S. PATENT DOCUMENTS 4,696,810 A  *  9/1987  Shirasaki et al.
5,112,433 A  *  5/1992  Dawson et al.
5,244,753 A  *  9/1993  Taniguchi et al.
6,004,688 A  * 12/1999  Goodenough et al.

* cited by examiner

Primary Examiner—Stanley S. Silverman
Assistant Examiner—Christina Ildebrando
(74) Attorney, Agent, or Firm—Burns, Doane, Swecker & Mathis, L.L.P.

(57) ABSTRACT

The present invention relates to a compound of the LaMO3 type, M being aluminum, gallium or indium, in the form of a powder or in sintered form, its process of preparation and its use as an oxygen conductor. The compound in powder form is capable of achieving, by pressureless sintering, a density of at least 93% of the theoretical density and of giving a sintered compound substantially free of any electrically active secondary phase of the grain boundaries. The compound in powder form is obtained by the reaction of the salts of lanthanum and of the element M with a base, and then the separation and calcining of the precipitate obtained. It may also be obtained by mixing, in a liquid medium, salts of lanthanum, and of the element M and, optionally, of a base, and then spray-drying and calcining the precipitate obtained. The sintered compound may be used in any application requiring an oxygen-conducting material in oxide form, such as solid-oxide fuel cells.

8 Claims, No Drawings

LAMO₃ TYPE COMPOSITION, M BEING ALUMINIUM, GALLIUM OR INDIUM, IN POWDER OR SINTERED FORM, METHOD OF PREPARATION AND USE AS CONDUCTOR OF OXYGEN

This application is an application under 35 U.S.C. Section 371 of International Application Number PCT/FR97/02071, filed on Nov. 18, 1997.

The present invention relates to a compound of the $LaMO_3$ type, M being aluminium, gallium or indium, in powder form or in sintered form, its process of preparation and its use as an oxygen conductor.

At the present time, the fuel-cell field is experiencing a growth in development. However, the existing cells operate at high temperatures, of at least 900° C. At these temperatures, the phenomena of cation diffusion and reduction in the various elements of the cell introduce chemical reactions at the interfaces, followed by a deterioration in the electrical performance. Materials are therefore sought which allow the operating temperatures of these cells to be lowered. With regard to the solid electrolyte part, a compound of the (La,Sr) (Ga,Mg) $O_3$ type is known which has, for intermediate temperatures lying between 700 and 900° C., a useful ionic conductivity that is higher than that of the yttriated zirconia normally used. However, this type of product can be obtained in sintered form at a suitable density only by pressure sintering (HIP). Furthermore, it has also not been possible hitherto to obtain this type of product with, in addition, a phase purity of greater than 80–90%. Thus, spurious phases appear at the grain boundaries during sintering. These spurious phases block the diffusion of $O^{2-}$ ions in the final solid electrolyte system, which entails a reduction in electrical performance.

There is therefore a need for a product which can be obtained in sintered form by the simpler process of pressureless sintering.

There is also a need for a product having an improved phase purity.

One object of the present invention is to provide products which satisfy these needs.

Another object of the invention is to provide precursors for such products.

To this end, the precursor compound of the invention is of the $LaMO_3$ type, M being aluminium, gallium or indium, and it is characterized in that it is in the form of a powder capable of achieving, by pressureless sintering, a density of at least 93% of the theoretical density and of giving, after sintering, a product substantially free of any electrically active secondary phase at the grain boundaries.

Moreover, the invention relates to a sintered compound of the $LaMO_3$ type, M being aluminium, gallium or indium, which is characterized in that it is substantially free of any electrically active secondary phase at the grain boundaries and in that it is obtained by pressureless sintering.

In the two compounds described above, the lanthanum and the gallium may be partially substituted.

The invention also relates to a process for the preparation of a precursor compound of the aforementioned type.

According to a first version, the process of preparation of the invention is characterized in that salts of lanthanum and of the element M and, optionally, salts of the substituents for the element M and for the lanthanum are made to react with a base, by means of which. a precipitate is obtained, the precipitate is separated from the reaction mixture and the precipitate is calcined.

According to a second version, the process of preparation is characterized in that a mixture of salts of lanthanum and of the element M and, optionally, of salts of the substituents for the element M and for the lanthanum is formed in a liquid medium; the said mixture is spray-dried and the product obtained is calcined.

According to a third version, the process of preparation is characterized in that a mixture of, on the one hand, a base and, on the other hand, of salts of lanthanum and of the element M and, optionally, of salts of the substituents for the element M and for the lanthanum is formed in a liquid medium; the mixture obtained is sprayed and the product coming from the spraying operation is calcined.

Finally, the invention also relates to a device incorporating an oxygen-conducting solid-electrolyte material in oxide form, of the type such as an oxygen probe, a fuel cell, a membrane-type chemical reactor or an oxygen separation membrane, characterized in that it comprises a sintered compound according to the invention.

Further features, details and advantages of the invention will become even more apparent on reading the description which follows, as well as from the concrete but non-limiting examples intended to illustrate it.

Firstly, the compound of the invention called the precursor compound, i.e. the compound capable of giving-the sintered compound by sintering, will be described.

This compound is in the form of a powder.

In general, this powder has a particle size of at most 10 $\mu$m, more particularly at most 5 $\mu$m and even more particularly at most 2 $\mu$m. The particle size given here corresponds to the average size of the particles forming the powder and measured by the technique of laser scattering, using a particle size analyser of the CILAS HR 850 type (volume distribution).

The precursor compound of the invention is characterized by its sintering behaviour. In fact, it is capable of reaching, by pressureless sintering, a density of at least 93% of the theoretical density. According to a preferred version, it is capable of reaching, under the same conditions, a density of at least 95% of the theoretical density. The density given here is that obtained after sintering in air, at 1500° C., for 6 hours.

It is mentioned here, and with regard to the entire description, that the density is determined by the use of the buoyancy principle on sintered pills immersed in a petroleum medium.

The other specific characteristic of the sintering behaviour of the precursor compound of the invention is the fact that this precursor is also capable of giving, after sintering, and especially after pressureless sintering, a sintered product substantially free of any electrically active secondary phase at the grain boundaries.

The expression "electrically active phase" should be understood to mean any phase capable of having an influence on the electrical properties of the compound in question.

This absence of an electrically active secondary phase at the grain boundaries may be demonstrated by measuring the ionic conductivity of the sintered compound.

The absence of an electrically active secondary phase at the grain boundaries may also be demonstrated by the method of complex impedance spectroscopy carried out in air (as described by J. E. BAUERLE, J. Phys. Chem. Solids, 30 (1969), 2657). This method gives idealized complex impedance plots (Nyquist plots) giving the imaginary part of the impedance as a function of its real part. The plots obtained for the compounds of the invention after sintering demonstrate a lack of response due to the grain boundaries (a semicircle, corresponding to an equivalent electrical circuit whose capacitance would be between $10^{-11}$ and $10^{31\ 8}$ farads, is not observed).

Finally, it is mentioned here that the expression "substantially free" should be understood to mean that it is impossible to demonstrate the presence of electrically active secondary phases on account of the limits for the detection of such phases using the method that has just been given.

As indicated above, the precursor compound satisfies a formula of the $LaMO_3$ type, in which M may be aluminium, gallium or indium or else a combination of at least two of these elements.

According to one particular embodiment, the element M is gallium.

According to another particular embodiment, the lanthanum is partially substituted with an alkali metal, an alkaline-earth metal or a rare earth. The expression "rare earth" should be understood to mean the elements of the group consisting of yttrium and the elements of the Periodic Table having an atomic number of between 57 and 71 inclusive. The alkali metal may be, in particular, sodium or potassium. The alkaline-earth metal may more particularly be strontium. Sodium and potassium allow particularly high densities to be obtained after sintering.

The element M, especially gallium, may also be partially substituted with an alkaline-earth metal or with zinc. As an alkaline-earth metal substituting for the element M, mention may be made of magnesium.

The proportions of substituents for the lanthanum and for the element M may vary widely. In the case of lanthanum and of a lanthanum substituent of the alkali metal or alkaline-earth metal type, the substituent/lanthanum atomic ratio may preferably range up to 10%, or alternatively up to 25%. When the lanthanum substituent is a rare earth, this ratio may range up to 80%. In the case of the element M, the substituent/M atomic ratio may preferably range up to 40%.

Finally, it will be noted within the context of the present invention that the lanthanum and the element M may each be partially substituted with one or more substituents of the type described above.

The compound of the invention in sintered form will now be described.

This compound is characterized in that it is substantially free of any electrically active secondary phase at the grain boundaries. Of course, everything that was described above with regard to the absence of these secondary phases applies here to the description of the sintered product.

The sintered compound of the invention may also be characterized in that it is obtained by pressureless sintering. The density of the sintered compound is preferably at least 93% of the theoretical density. This density may even be at least 95%. Densities of at least 97% of the theoretical density may be reached.

The sintered compound satisfies a formula of the $LaMO_3$ type, but what was described earlier with regard to the partial substitution of the lanthanum and M elements also applies here.

The absence of an electrically active secondary phase at the grain boundaries gives the sintered compounds of the invention a high ionic conductivity. In the case of the compounds containing strontium and magnesium as the respective partial substituents for the lanthanum and for the gallium, this conductivity is at least 0.005 S/cm at 600° C. It may more particularly be at least 0.015 S/cm. The conductivities mentioned here are determined from AC complex impedance measurements. The sintered compounds of the invention also have a conductivity of at least 0.04 S/cm and preferably at least 0.06 S/cm at 800° C. For this temperature, the conductivities are measured in air using the DC 4-point method. These conductivity measurements apply throughout the description.

The sintered compound may have a cubic, orthorhombic or tetragonal structure. This phase may be pure. In the particular case of the compound of formula $La_{0.9}Sr_{0.1}Ga_{0.8}Mg_{0.2}O_{2.85}$, this may be in the form of a single pure phase corresponding to a tetragonal perovskite system.

The processes for the preparation of the compounds of the invention will now be described.

A first version of the process for the preparation of a precursor compound may be considered.

This process comprises a first step in which salts of lanthanum and of the element M and, optionally, salts of the substituents for the element M and for the lanthanum are made to react with a base. This reaction takes place in a liquid medium. The reaction with the base gives a precipitate. The precipitate is separated from the reaction mixture by any suitable means. The precipitate is then calcined.

A second version of the process of the invention also exists which is particularly suitable for the preparation of a compound with substituents. This process firstly consists in forming a mixture of salts of lanthanum and of the element M and, optionally, of salts of the substituents for these elements in a liquid medium. Next, in a second step, this mixture is subjected to a spraying operation.

The term "spray-drying" should be understood to mean drying by spraying the mixture in a hot atmosphere. The spraying may be carried out by means of any spraying device known per se, for example using a spray nozzle of the sprinkler-rose type or of another type. It is also possible to use so-called turbine atomizers. With regard to the various spraying techniques that can be used in the present process, reference may be made especially to the fundamental work by Masters entitled "SPRAY-DRYING" (second edition, 1976, published by George Godwin, London).

In a final step, the sprayed product obtained is calcined.

A third version of the process may be mentioned which is also particularly suitable for the preparation of a compound with substituents. According to this version, a mixture of, on the one hand, a base and, on the other hand, of salts of lanthanum and of the element M and, optionally, of salts of the substituents for these elements is firstly formed in a liquid medium. During the formation of this mixture, the base reacts with the salts and a mixture comprising a precipitate resulting from this reaction between the base and the salts is obtained. The remainder of the process is identical to that of the process according to the previous version; in fact, the mixture obtained is sprayed and the product coming from the spraying operation is calcined.

A fourth and final version will be described which applies very particularly to the preparation of a compound in which the lanthanum is partially substituted with an alkaline-earth metal chosen from strontium, calcium and barium.

The process according to this version includes a first part in which a compound containing all the constituent elements apart from the lanthanum substituent is firstly formed. To do this, in a first step, salts of lanthanum and of the element M and, optionally, salts of the substituents for this element, if these substituents are other than strontium, calcium and barium, are made to react with a base.

In a second step, the precipitate obtained by this reaction is separated from the reaction mixture. Next, the precipitate undergoes a first calcining operation.

In a second part of the process, a mixture of a salt of the alkaline-earth metal substituting for the lanthanum and of the product coming from the above calcining operation is formed in a liquid medium.

The mixture or compound thus obtained is sprayed. It will be noted that what was described above with regard to spraying in the case of the second version of the process also applies here for this spraying step of the present version.

Finally, the product coming from the spraying operation undergoes a final calcining operation.

In the context of this same version, the first part of the process may also be carried out a different manner. Thus, a mixture of salts of lanthanum and of the element M and, optionally, of salts of the substituents for the element M, if these substituents are other than strontium, calcium and barium, is formed in a liquid medium. Next, the mixture thus obtained is sprayed. Thereafter, a first calcining operation is then carried out in which the product coming from this spraying operation is calcined. The calcined product obtained after this first part is then mixed, in a liquid medium, with the salt of the alkaline-earth metal substituting for the lanthanum and the process according to a second part, identical to that which has just been described, is carried out.

Moreover, the first part of the process according to this fourth version may be carried out in a manner similar to that described in the case of the third version. In fact, in this case, a mixture of salts of lanthanum and of the element M and of a base is formed in a liquid medium, it being possible for the liquid medium to also contain, optionally, salts of the substituents for the element M if these substituents are other than strontium, calcium and barium. The mixture thus obtained, which comprises the precipitate resulting from the reaction between the base and the salts, is sprayed and then subjected to a first calcining operation in which the product coming from this spraying operation is calcined. The second part of the process is then identical to that described above with regard to this fourth version.

Finally, it is also possible within the context of this fourth version to proceed in the following manner. In a first part, a compound containing all of the constituent elements apart from the lanthanum substituent is firstly formed, as was described above. In a second part, the compound thus formed is then mixed and calcined with a calcined compound in oxide form containing both the alkaline-earth metal and the element M. This compound in oxide form may, for example, be $Sr_2Ga_2O_5$. Next, the mixture is sprayed and then calcined.

Further details will now be given with regard to the steps common to the various process versions that have just been described.

The liquid media mentioned above are generally aqueous media.

The salts of the various elements may be inorganic or organic salts. Preferably, salts soluble or partially soluble in water are used. By way of example, mention may be made of nitrates and chlorides. The amounts of salts used are determined in order to satisfy the stoichiometric proportions required for obtaining the desired final compound.

The base is preferably used in the form of a liquid solution. An aqueous ammonia solution or ammonium hydrogen carbonate solution may most particularly be used. The aforementioned reaction between base and salts may be carried out, or the aforementioned mixture of the salts with the base may be formed, either by introducing the salts, in the form of a first solution, into a second solution containing the base, or vice versa, or by introducing the salts and the base together, for example into a stock of water. Furthermore, the mixing may be carried out or the reaction conducted while keeping the pH of the reaction mixture constant. The pH may be kept at a constant value by adding, at the same time as the salts, a sufficient amount of base to the mixture or to the reaction mixture.

The aforementioned reaction or the mixing is carried out at a temperature which may range from room temperature up to the boiling point of the reaction mixture. It may be advantageous to work at a temperature of between 40 and 60° C.

When the mixing is carried out or the reaction conducted at a constant pH, the pH value may advantageously be fixed between 7 and 12, preferably between 9 and 11.

Once the reaction or the mixing has been carried out, it may also be advantageous to leave the reaction mixture to age, particularly by maintaining temperature and pH conditions identical to those at which the reaction or the mixing took place. This ageing may last, for example, from 30 minutes to 5 hours.

In the case of the first version, which does not include a spraying step, the separated precipitate may be washed with water or optionally with a basic solution, for example an aqueous ammonia solution, and then dried.

The calcining is carried out at a temperature high enough and for a time long enough to obtain the phase sought. Consequently, depending on the compound sought, this temperature may be between 700 and 1600° C. The calcining time is usually between 2 and 6 hours. The calcining may optionally be carried out in several steps at different temperatures. Furthermore, part of the calcining operation may be carried out in a reducing atmosphere in order to promote the formation of a powder able to give a pure phase after sintering.

It will be noted in the fourth version that the first calcining operation takes place at the temperature necessary for preforming the $La_{1-x}(M,M')O_{3-y}$ type phase, y<3 and M' denoting the optional substituent for M, other than strontium, calcium and barium, that is to say generally a temperature of between 400 and 900° C.

Finally, in the context of the fourth version, it is possible to carry out the calcining according to the embodiment which has just been described (calcining between 600 and 1200° C. and then between 1400 and 1600° C.) and to complete this calcining with a final calcining operation in a reducing atmosphere, especially an atmosphere consisting of a mixture of hydrogen and of an inert gas such as argon and at a temperature which may be between 1000 and 1200° C.

The various process versions which have just been described result in the precursor product of the invention, that is to say the product in the form of a powder. If necessary, the powder thus obtained may be ground. Thus, grinding may be carried out in a wet medium or by ultrasound. It is advantageous to obtain powders with an average size of the order of one micron.

The sintering of the precursor compound of the invention, such as the one described above or such as the one obtained by the process previously studied, is carried out in a manner known per se. The precursor compound is firstly formed. This forming operation may be carried out by pressing, for example by uniaxial pressing, by calendering or by tape casting. For the forming operation, a binder of known type such as, in particular, polyvinyl alcohol, resins (for example of the "carbowax" type), metal stearates, such as aluminium and zinc stearates, sugars, starches, alginates and polymethylphenylene may be used. The component thus formed is then pressurelessly sintered at a temperature high enough to obtain the desired density. Usually, this temperature is between approximately 1500° C. and approximately 1550° C. Generally, the sintering is carried out in air. The duration may vary from 2 to 30 hours depending on the density that it is desired to obtain. The precursor compounds of the invention have very good sinterability. They may, for example, give products sintered to 93% after 2 hours of sintering at 1500° C.

Depending on its properties, the sintered product of the invention may advantageously be used in any application requiring a material, in oxide form, which is a solid electrolyte and an oxygen conductor. Thus, it may be incorporated into oxygen probes, for example λ probes, for regulating exhaust gases, in solid-oxide fuel cells, in membrane-type chemical reactors, for example reactors for the controlled oxidation of hydrocarbons, or else in oxygen separation membranes. The invention therefore relates to devices, of the aforementioned type, comprising a sintered compound according to the invention.

Examples will now be given.

EXAMPLE 1

This example relates to the synthesis of the compound $La_{0.9}Sr_{0.1}Ga_{0.8}Mg_{0.2}O_{2.85}$. The salts used are as follows:

$Sr(NO_3)_2$ $Mg(NO_3)_2.6H_2O$ $La(NO_3)_3.6H_2O$ $Ga(NO_3)_3.6H_2O$.

0.15 mol of the compound $La_{0.9}Ga_{0.8}Mg_{0.2}O_{2.75}$ is prepared by introducing a solution containing lanthanum, gallium and magnesium nitrates (0.75N solution) in the necessary amounts into a stirred aqueous ammonia solution maintained at 50° C. While the salt solution is being introduced, the pH is maintained constant at a value of 9 by simultaneously adding an 11N aqueous ammonia solution. Next, the mixture obtained is left to age for 1 hour at the same temperature and at the same pH.

The mixture obtained (precipitate and mother liquors) is sprayed using a Büchi® atomizer, The entry temperature of the solid is 150° C. and the exit temperature is 110° C. Thus a powder of dried hydroxides is obtained.

This powder is calcined at 400° C. in air for 2 hours (temperature rise at 300° C./h).

The calcined powder is suspended in water and then strontium nitrate is added in stoichiometric proportions to this suspension.

This suspension is sprayed under the same conditions as those given above and then calcined at 900° in air for 2 hours (temperature rise at 300° C./h). The powder has a particle size (as defined and measured above) of 9 μm.

1 cm² pills are formed by uniaxially pressing 0.8 g of powder at 2 tonnes/cm². The pills undergo pressureless sintering in air at 1500° C. for 2 hours, 6 hours and 30 hours, respectively. The densities obtained are 93%, 94% and 97%, respectively.

The product of formula $La_{0.9}Sr_{0.1}Ga_{0.8}Mg_{0.2}O_{2.85}$ is obtained. Analysis of the X-ray spectrum of this product shows that it is present in the form of a pure phase in a tetragonal system having unit cell parameters a=5.533 Å and c=7.827 Å. Complex impedance spectroscopy shows that there is no electrically active secondary phase at the grain boundaries. The measured conductivity is 0.029 S/cm at 600° C. and 0.08 S/cm at 800° C.

The powder of 9 μm particle size obtained above is ground wet with zirconium balls in order to obtain a particle size of 1.3 μm. Next, the forming and sintering operations are carried out as described above. After sintering at 1500° C. for 2 hours, the product has a density of 98%.

EXAMPLE 2

This example relates to the synthesis of the compound $La_{0.95}Na_{0.05}Ga_{0.8}Mg_{0.2}O_{2.85}$.

Raw Materials Used 99.99% $La(NO_3)_3$ in solution, c=2.8 m/l, rd=1.70

$Ga(NO_3)_3$ in solution, c=1.807 m/l, rd=1.362

Crystallized 97% $Mg(NO_3)_2$, MW=256.41

Crystallized 99.5% $NaNO_3$, MW=84.99

22% $NH_4OH$ solution, MW=17.03.

Preparation

The preparation comprises the following steps:

A) Synthesis by ammoniacal coprecipitation of $La_{0.95}Ga_{0.8}Mg_{0.2}O_x$ by introducing a 0.75 m/l solution containing the nitrates (200 ml) into a stock (500 ml at pH 9) at a rate of 3.3 ml/minute; pH 9 regulation using 22% $NH_4OH$ and then ageing for 1 hour at 50° C.

B) Spraying the entire mother liquors+precipitate material (entry temperature: 240° C., exit temperature 110° C.).

C) Calcining at 400° C. (2 hours, temperature rise at 5° C./minute).

D) Spraying the $La_{0.95}Ga_{0.8}Mg_{0.2}O_x$ with the necessary amount of $NaNO_3$ (entry temperature: 240° C., exit temperature: 110° C.).

E) Calcining: 2 hours at 900° C. (temperature rise at 5° C./minute).

F) Wet grinding so as to obtain a particle size of between 1 and 2 μm.

After forming and sintering under the same conditions as those given for Example 1, a product is obtained which has the following density (d) and conductivity (σ) characteristics at 600° C. and 800° C.:

d=98.7% (1500° .C/6 h) $\sigma_{600}$=0.007 S/cm (AC) $\sigma_{800}$= 0.047 S/cm (DC).

An analysis of the X-ray spectrum of the product shows that it is present in the form of a pure phase in an orthorhombic system having unit cell parameters a=5.488 Å, b=5.536 Å and c=7.804 Å. Complex impedance spectroscopy shows that there is no electrically active secondary phase at the grain boundaries.

EXAMPLE 3

This example relates to the synthesis of the compound $La_{0.95}K_{0.05}Ga_{0.8}Mg_{0.2}O_{2.85}$.

Raw Materials 99.99% $La(NO_3)_3$ in solution, c=2.8 m/l, rd=1.70

$Ga(NO_3)_3$ in solution, c=1.807 m/l, rd=1.362

Crystallized 97% $Mg(NO_3)_2$ MW=256.41

Crystallized 99.5% $KNO_3$, MW=101.1

22% $NH_4OH$ solution, MW=17.03.

Preparation

The preparation comprises the same steps as in Example 2, except that, at step D, $KNO_3$ is added instead of $NaNO_3$.

A product having the following characteristics is obtained:

d=99.8% (1500° C./6 h)

$\sigma_{600}$=0.008 S/cm (AC)

$\sigma_{800}$=0.074 S/cm (DC).

An analysis of the X-ray spectrum of the product shows that it is in the form of a pure phase in an orthorhombic system having unit cell parameters a=5.510 Å, b=5.536 Å and c=7.808 Å. Complex impedance spectroscopy shows that there is no electrically active secondary phase at the grain boundaries.

EXAMPLE 4

This example relates to the preparation of a product satisfying the general formula $La_{0.9}Sr_{0.1}Ga_{0.8}Mg_{0.2}O_{2.85}$ from the two compounds $LaGa_{0.77}Mg_{0.23}O_3$ and $Sr_2Ga_2O_5$ which are used in the necessary stoichiometric proportions.

Raw Materials 99.99% $La(NO_3)_3$ in solution at 2.762 m/l, rd=1.6816

$Ga(NO_3)_3$ in solution at 1.807 m/l, rd=1.365

Crystallized 98% $Mg(NO_3)_2$, MW=256.41

Crystallized 99% $Sr(NO_3)_2$, MW=211.63.

Preparation

The two phases are prepared separately by codrying the combination of the suitable elements.

A) $LaGa_{0.77}Mg_{0.23}O_3$ obtained by spray-codrying the raw materials (entry temperature: 220° C.; exit temperature: 140° C.; rate: 5 ml/minute).

B) Compound of general formula $Sr_2Ga_2O_5$ obtained by spray-codrying the raw materials at temperatures identical to those given in A).

C) Calcining the two precursors at 400° C. (2 hours, temperature rise at 5° C./minute).

D) Grinding the mixture of the two precursors in an amount necessary to form the product.

E) Spraying the entire material (entry temperature: 220° C.; exit temperature: 120° C.; rate: 8 ml/minute).

F) Calcining: 2 hours at 900° C., 5° C./minute.

A product having the following characteristics is obtained:

d=94% (1500° C./6 h) $\sigma_{600}$=0.019 S/cm (AC) $\sigma_{800}$=0.13 S/cm (DC).

Analysis of the X-ray spectrum of this product shows that it is in the form of a pure phase in a tetragonal system having unit cell parameters a=5.537 Å and c=7.832 Å. Complex impedance spectroscopy shows that there is no electrically active secondary phase at the grain boundaries.

EXAMPLE 5

This example relates to the preparation of the product satisfying the formula $La_{0.8}Sr_{0.2}Ga_{0.8}Mg_{0.2}O_{2.85}$.

Raw materials 99.99% $La(NO_3)_3$ in solution at 2.762 m/l, rd=1.6816

$Ga(NO_3)_3$ in solution at 1.807 m/l rd=1.365

Crystallized 99% $Sr(NO_3)_2$, MW=211.63

Crystallized 98% $Mg(NO_3)_2$, MW=256.41.

Preparation

The Mg and Sr salts are dissolved in the mixture of the La and Ga salts, with stirring.

The solution thus obtained is sprayed (entry temperature: 220° C.; exit temperature: 140° C.) at a rate of 5 ml/minute.

Calcining is carried out for 2 hours at 400° C. (temperature rise 5° C./minute) and then 2 hours at 900° C. (temperature rise 5° C./minute).

Wet grinding is carried out in order to obtain a particle size of between 1 and 2 μm.

A product having the following characteristics is obtained:

d=93% (1500° C./6 h) $\sigma_{600}$=0.015 S/cm (AC) $\sigma_{800}$=0.096 S/cm (DC).

Analysis of the X-ray spectrum of this product shows that it is in the form of a pure phase in a cubic system having a unit cell parameter a=3.914 Å. Complex impedance spectroscopy shows that there is no electrically active secondary phase at the grain boundaries.

What is claimed is:

1. A process for the preparation of a sintered compound having grain boundaries, of formula: $LaMO_3$, M being aluminum, gallium or indium and wherein the lanthanum is partially substituted with an alkali metal, an alkaline-earth metal or a rare earth and the element M is partially substituted with an alkaline-earth metal or zinc, wherein said compound is substantially free of any electrically active secondary phase at the grain boundaries, and is obtained by pressureless sintering, said process comprising the steps of:
   a) forming a mixture of salts of lanthanum and of the element M and of salts of the substituents for the element M and for the lanthanum in a liquid medium,
   b) spray-drying said mixture to obtain a product, and
   c) calcining the product obtained in step b).

2. A process for the preparation of a sintered compound having grain boundaries, of formula: $LaMO_3$, M being aluminum, gallium or indium and wherein the lanthanum is partially substituted with an alkali metal, an alkaline-earth metal or a rare earth and the element M is partially substituted with an alkaline-earth metal or zinc, wherein said compound is substantially free of any electrically active secondary phase at the grain boundaries, and is obtained by pressureless sintering, said process comprising the steps of:
   a) forming in a liquid medium a mixture of a base and salts of lanthanum and the element M and salts of the substituents for the element M and for the lanthanum;
   b) spray-drying the mixture obtained in step a) to obtain a product, and
   c) calcining the product obtained in step b).

3. A process for the preparation of a sintered compound of formula: $LaMO_3$, M being aluminum, gallium or indium and wherein the lanthanum is partially substituted with an alkali metal, an alkaline-earth metal or a rare earth and the element M is partially substituted with an alkaline-earth metal or zinc, wherein said compound is obtained by pressureless sintering a powder constituted by grains, and is substantially free of any electrically active secondary phase at the grain boundaries, and wherein the lanthanum is partially substituted with an alkaline-earth metal selected from the group consisting of strontium, calcium and barium, said process comprising the steps of:
   a) reacting with a base salts of lanthanum and of the element M and, optionally, salts of the substituents for this element, if these substituents are other than strontium, calcium and barium to obtain a precipitate in a reaction mixture,
   b) separating the precipitate from the reaction mixture;
   c) calcining the precipitate in a first calcining operation;
   d) forming in a liquid medium a mixture of the calcined precipitate of step c) and of a salt of the alkaline-earth metal substituting for the lanthanum to obtain a mixture;
   e) spray-drying the mixture of step d) to obtain a product; and
   f) carrying out a second calcining operation on the product obtained in step e).

4. A process according to claim 3, wherein the calcined precipitate of step (c) is further mixed with a calcined compound in oxide form containing both the alkaline-earth metal and the element M, and, then, the mixture thus obtained is further sprayed and calcined.

5. A process according to claim 3, wherein the lanthanum is partially substituted with Strontium, Calcium, or Barium.

6. A process for the preparation of a sintered compound having grain boundaries, of formula: $LaMO_3$, M being aluminum, gallium or indium and wherein the lanthanum is partially substituted with an alkali metal, an alkaline-earth metal or a rare earth and the element M is partially substituted with an alkaline-earth metal or zinc, wherein said compound is substantially free of any electrically active secondary phase at the grain boundaries, and is obtained by pressureless sintering, and wherein the lanthanum is partially substituted with an alkaline-earth metal selected from the group consisting of strontium, calcium and barium, said process comprising the steps of:

(a') forming a mixture of salts of lanthanum and of the element M and, optionally, of a base in a liquid medium, it being possible for the liquid medium to also contain, optionally, salts of the substituents for the element M if these substituents are other than strontium, calcium and barium;

(b') spraying the mixture of step (a') to obtain a product;

(c') carrying out on the product obtained in step (b') a first calcining operation to obtain a calcined product;

(d') forming a mixture of the calcined product obtained in step (c') and of a salt of the alkaline-earth metal substituting for the lanthanum, in a liquid medium;

(e') spray-drying the mixture obtained in step (d') to obtain a product; and (f') undergoing a second calcining operation on the product obtained in step (e').

7. A process according to claim 6, wherein the product obtained at the aforementioned step (c') is further mixed with a calcined compound in oxide form containing both the alkaline-earth metal and the element M, and then the mixture thus obtained is sprayed and calcined.

8. A process according to claim 6, wherein the lanthanum is partially substituted with Strontium, Calcium, or Barium.

* * * * *